(12) United States Patent
Favre-Bulle et al.

(10) Patent No.: US 7,247,462 B2
(45) Date of Patent: Jul. 24, 2007

(54) COATED ENZYME-CONTAINING CATALYST

(75) Inventors: Olivier Favre-Bulle, Nimes (FR); Jean-Claude Le Thiesse, Saint-Etienne (FR)

(73) Assignee: Adisseo Ireland Ltd (IE)

( * ) Notice: Subject to any disclaimer, the term of this patent is extended or adjusted under 35 U.S.C. 154(b) by 399 days.

(21) Appl. No.: 10/311,951

(22) PCT Filed: Jun. 22, 2001

(86) PCT No.: PCT/EP01/09875

§ 371 (c)(1),
(2), (4) Date: Nov. 24, 2003

(87) PCT Pub. No.: WO02/00869

PCT Pub. Date: Jan. 3, 2002

(65) Prior Publication Data

US 2004/0082046 A1    Apr. 29, 2004

(30) Foreign Application Priority Data

Jun. 30, 2000    (EP) ................................ 00113861

(51) Int. Cl.
*C12P 7/62*    (2006.01)
*C12N 11/14*    (2006.01)
*C12N 11/04*    (2006.01)
*C12N 9/98*    (2006.01)
*C12N 9/96*    (2006.01)
*C12N 1/20*    (2006.01)
*C12N 15/00*    (2006.01)

(52) U.S. Cl. ...................... 435/135; 435/176; 435/182; 435/187; 435/188; 435/455

(58) Field of Classification Search .................... None
See application file for complete search history.

(56) References Cited

U.S. PATENT DOCUMENTS 6,180,359 B1 * 1/2001 Favre-Bulle et al. .......... 435/41
6,214,592 B1 * 4/2001 Crouzet et al. ............. 435/129

* cited by examiner

Primary Examiner—David M. Naff
(74) Attorney, Agent, or Firm—Connolly Bove Lodge & Hutz LLP

(57) ABSTRACT

An enzymatic catalyst in the granular form which is non-dispersible in water comprising an inner core provided with a coating which coating comprises an enzymatic material characterised in that the coating has a thickness of from 30 to 400 microns and the ratio of the size of the core to the thickness of the coating is from 2 to 20. A method for the preparation of the catalyst and the use of the catalyst in the conversion of 2-hydroxy-4-methylthio butyronitrile to ammonium 2-hydroxy-4-methylthio butanoate is also claimed.

12 Claims, No Drawings

COATED ENZYME-CONTAINING CATALYST

FIELD OF THE INVENTION

The present invention relates to an enzymatic catalyst and in particular to an enzymatic catalyst in the granular form wherein the granule is provided with a coating comprising the enzyme.

BACKGROUND OF THE INVENTION

Compositions comprising immobilised cells having enzymatic activity are known, for example in European Patent No. 0089165 which discloses a composition wherein a coating comprising *E. coli* which is fixed by means of a cross-linked polymer is on an inert carrier. This composition is used to prepare L-aspartic acid. European Patent Application No. 0297912 also discloses a biologically active material which comprises a coated particle wherein the coating comprises a the biological material and a cross-linked polymer.

SUMMARY OF THE INVENTION

We have found that a coated granular enzymatic material having a specific thickness of coating with regard to the inner core of the granule to which the coating is applied, shows unusual beneficial advantages over the known enzymatic catalyst materials.

Accordingly, the present invention provides an enzymatic catalyst in the granular form which is non-dispersible in water, said catalyst comprising an inner core provided with a coating which coating comprises an enzymatic material characterised in that the coating has a thickness of from 30 to 400 microns and the ratio of the size of the core to the thickness of the coating is from 2 to 20.

The enzymatic catalyst of the present invention provides the advantage over the prior art in that where the thickness of the coating is controlled, the resulting granular catalyst shows greater catalytic activity.

DETAILED DESCRIPTION OF THE INVENTION

The present invention is directed to an enzymatic catalyst in the granular form, hereinafter referred to as the granular enzymatic catalyst. The catalyst must be non-dispersible in water, preferably insoluble in water. This property is provided by the inner core, which is non dispersible in water and preferably insoluble in water. Suitable materials for use as the inner core include of alumina, silica, zeolites, resins, fatty substances such as stearic acid, glass beads and plastic beads. Preferably, the core is alumina.

The core may have any suitable shape for example regular or irregular spheres, oval and the like, although the preferred shape is a regular sphere with an average diameter of from 0.1 to 5 millimetres, preferably from 0.4 to 2.5 milimetres. The core may be either macroporous, mesoporous or microporous. Preferably, the core is not macroporous so as to avoid entry of the enzymatic material into the pores.

The coating of the core has a thickness of from 30 to 400 microns, preferably from 100 to 250 microns. The ratio of the size of the core to the thickness of the coating is from 2 to 20, preferably from 3 to 15. For the purposes of the present invention, the size of the core is defined as the maximum internal diameter, namely the greatest distance between two outer points on the peripheral wall of the core.

The coating of the granular catalyst comprises an enzymatic material. The enzymatic material may be enzymes soluble or cell bound alike, microorganisms (intact or disrupted cells viable or non-viable), antibodies and coenzymes or a mixture thereof. Particularly suitable enzymatic materials include glucose isomerases, penicillin aceylases, nitrile hydratases, nitrilases, amideases, lipases, proteases and esterases. The preferred enzymatic material is nitrilases.

In addition to the enzymatic material, it is preferred that the coating further comprises a polymer and a cross-linking agent. The presence of these compounds permits the enzymatic material to be embedded in the cross-linked network of the polymer. This network overcomes one of the major problems with immobilization, namely the leakage of desired enzymes from the immobilizing material. It is, therefore, useful to make the confinement barrier impermeable to high molecular weight species. Suitable, polymers include polyazetidine polymers, polyamine polymers such as polyethyleneimine, polyamide polymers such as proteins, isocyanate polymers or a mixture thereof The preferred polymer is a polyazetidine polymer as it affords good mechanical strength for the coating layer. Examples of polyazetidine polymers which may be used are the commercially available polymers such as Polycup 2002. Kymene 617 and Kymene 450 (all brand names of Hercules Inc., USA). Suitable cross-linking agents include amines such as hexamethylenediamine, aldehydes such as glutaraldehyde or acrolein, acids such as adipic acid, isocyanates such as hexamethylene diisocyanate. The preferred cross-linking agent is glutaraldehyde. A particularly preferred coating for the purpose of the present invention is a mixture of nitrilases, a polyazetidine polymer and glutaraldehyde.

As regards the amount of enzymatic material, polymer and cross-linking agent in the coating of the catalytic material, the amount of each component in the dry coating is suitably from 50 to 80%, preferably from 40 to 60% of enzymatic material; suitably from 5 to 20%. preferably from 10 to 15% of polymer material and suitably from 1 to 5%, preferably from 2 to 3% of cross-linking, agent. Additional components may also be present in the coating, such as polyols, for example glucose, sucrose, trehalose, maltitol, sorbitol and glycerol, and/or salts, for example phosphate. These can be present in an amount of from 0 to 35%. The coating may also comprise a finite amount of water. Suitably, water is present in an amount of from 0 to 30% of the coating.

The enzymatic catalyst of the present invention may be prepared by any suitable immobilisation method known to the person skilled in the art, for example by gel entrapment or adsorption. European Patent Applications 0297912, 0206687 and 0502035 disclose a procedure wherein an aqueous mixture containing the enzymatic material is deposited by absorption on to the granule. The granule is then dried. An alternative method for the deposition of the coating is as disclosed in EP089165 which involves forming a paste containing the enzymatic material, applying the paste to the granule and then drying the resulting granule.

We have found that coated granular enzymatic catalysts also can be prepared by spraying the core with a mixture of the coating material and thus according to another aspect of the present invention there is provided a process for the preparation of an enzymatic catalyst as herein before described which process comprises forming an aqueous suspension of an enzymatic material, a polymer and a cross-linking agent and spraying said suspension on to the core, thereby coating said core.

The preparation of the coated enzymatic catalyst using the spraying technique, generally referred to as "spray coating", provides the advantage over other known immobilisation methods in that the thickness of the coating can be controlled to provide the desired thickness, this being an important feature of the enzymatic catalyst of the present invention.

To prepare the coated granular enzymatic catalyst using the spray coating technique, an aqueous suspension of the enzymatic material, the polymer and the cross-inking agent is used. The enzymatic material may used directly or may be purified prior to its use in the process of the present invention. It may be recovered by centifugation, filtration, precipitation, or flocculation. The enzymatic material may be washed with water or a water solution containing a salt such as sodium chloride, phosphate, EDTA or magnesium. A preferred starting material is the enzymatically active cell sludge recovered from a fermenter through the filtering or centrifuging the culture broth. The cell sludge may be used as such or it may be washed prior to use. The cells may be washed by diafiltration or by re-suspension and centrifugation.

The suspension may comprise 5-25% enzymatic material. 1-12% polymer and 0.2-4% cross-linking agent, these amounts being based on the total weight of the aqueous suspension. The amount of water in the suspension is not a critical factor and may be adapted by the person skilled in the art to the material used for spraying it. A solid content in the suspension of from 10 to 30% on a weight to volume basis is preferably used. The suspension may also comprise minor amounts of materials such as polyols for example glucose, sucrose, trehalose, maltitol, sorbitol and glycerol; and salts for example sodium chloride.

It is preferred, although not essential, to set the pH of the suspension at a value of between pH 5 and 9.5, most preferably between pH 7.5 and 8.5. To do so, a buffer may be used. Suitably, the buffer may be a phosphate, such as mono-or di-potassium phosphate or mono-or di-sodium phosphate; or a carbonate. The preferred buffer is a phosphate buffer. When a buffer is present in the suspension, between 15 and 50% by weight of buffer is added relative to the weight of the dry enzymatic material.

The suspension may be prepared by any suitable method. Preferably, the suspension is prepared by initially forming a suspension of the enzymatic material in either water or buffer. The cross-linking agent may then be added to the suspension of the enzymatic material. The cross-linking agent may be left in contact with the enzymatic material for a period which is sufficient to allow it to react with the amine, hydroxyl or carboxyl functions of the enzymatic material before addition of the polymer. Before performing the spraying step, optional agents such as polyols, the buffer and sodium chloride may be added to the suspension.

The suspension is suitably prepared at a temperature of between 0 and 50° C. and preferably between 10 and 35° C.

The suspension obtained then can be stored without any specific precaution for several days before being sprayed. The storage temperature will advantageously be between 0° C. and ambient temperature.

The suspension may be deposited on the core using any spray-coating device, preferably a bed of fluidized air. The air flow rate is suitably adjusted to obtain good fluidization of the solid support. The air inlet temperature is suitably adjusted to between 30 and 90° C. and the rate of spraying of the aqueous suspension is adjusted so as to keep the temperature of the bed between 10 and 60° C., preferably between 20 and 40° C. throughout the operation. The resulting layer of coating on the core has a thickness of between 30 and 400 microns.

The resulting enzymatic catalyst prepared according to the aforementioned method, can be stored for several months in water or a buffered medium or in the dry form prior to use.

The granular enzymatic catalysts of the present invention may be used in any suitable enzymatic process. In particular, the enzymatic catalyst of the present invention may be used in the conversion of 2-hydroxy4-methylthio butyronitrile (HMTBN) to the corresponding ammonium salt, namely ammonium 2-hydroxy-4-methylthio butanoate (HMTBS). The catalyst may also be used in the hydrolysis of NYLON 66 oligomers. A particular advantage of the catalyst of the present invention is that it exhibits greater half life than other known catalytic catalysts. In particular, the granular coated enzymatic catalyst shows a half life of at least 30 hours, preferably at least 70 hours.

The present invention will now be illustrated with reference to the following examples:

In the following examples, the following abbreviations are used:

HMTBN—2-hydroxy4-methylthio butyronitrile
HMTBS—ammonium 2-hydroxy4-methylthio butanoate

EXAMPLE 1

1.1 Preparation of the Enzymatic Catalyst:

Construction of the Strain *E. coli* BIOCAT 714

The 1.27 kb fragment containing the $P_{trp}$ promotor, the ribosome binding site of the phage cll gene (RBScII) and the nitrilase gene from *Alcaligenes faecalis* ATCC8750 (nitB) was extracted from the plasmid pRPA6BCAT6 (patent application WO 98/18941) using the restriction enzymes EcoRI and XbaI, then cloned in the vector $pXL^{642}$ (described in U.S. Pat. No. 5,629,190) opened with the same restriction enzymes. The resulting plasmid, pRPA-BCAT15 was opened with the enzymes StuI and BsmI and the 4.3 kb fragment was ligated with the purified 136 bp StuI-BsmI fragment from pRPA-BCAT4 (patent application WO 98/18941) to give the plasmid pRPA-BCAT19. Partial sequencing of pRPA-BCAT19 confirmed the replacement of the codon for the Asp279 residue of nitrolase with the codon for an Asn279 residue. The 1.2 kb EcoRI-XbaI fragment from pRPA-BCAT19 containing the $P_{trp}$::RBScII::nitB fusion was then cloned in the vector pRPA-BCAT28 opened with the same enzymes, to give the 6.2 kb plasmid pRPA-BCAT29. The vector pRPA-BCAT28 was obtained by ligating the 3.9 kb SspI-ScaI fragment from pXL642 (CIP application No. 08/194,588) with the 2.1 kb SmaI fragment from pHP45 Tc (Fellay et al., 1987, Gene 52: 147-154) in order to replace the ampicillin resistance marker with the tetracycline resistance marker. By destroying the NdeI site close to the replication origin of the plasmid pRPA-BCAT29 by partial NdeI digestion and the action of the *E. coli* polymerase I (Klenow fragment), the plasmid pRPA-BCAT41 was obtained.

The plasmids pRPA-BCAT41 and pXL2035 (Levy-Schill et al., 1995, Gene 161: 15-20) were introduced into the *E. coli* strain W (ATCC9637) by standard electroporation. The clone obtained is referred to as BIOCAT 714.

Culturing of the Strain:

An *E. coli* W strain containing the nitrilase from *A. faecalis* ATCC8750 (BIOCAT 714) is cultured in a 100 liter fermenter containing 80 liters of medium whose composition is as given in Table 1:

TABLE 1

| Compound | Concentration in the medium (g/l) |
|---|---|
| $K_2HPO_4$ | 8 |
| $(NH_4)_2SO_4$ | 0.75 |
| $MgSO_4 \cdot 7H_2O$ | 2.5 |
| Iron sulfate | 0.04 |
| $CaCl_2 \cdot 2H_2O$ | 0.04 |
| Manganese sulfate | 0.026 |
| Cobalt chloride | 0.004 |
| Zinc sulfate | 0.013 |
| Sodium molybdate | 0.001 |
| Copper chloride | 0.001 |
| Boric acid | 0.00025 |
| $AlCl_3$ | 0.00125 |
| Citric•$H_2O$ | 1.7 |
| Glucose monohydrate | 2 |
| L-tryptophan | 0.1 |
| Yeast extract | 3 |
| Meat peptone | 5 |

The pH was maintained at 7.0 by adding aqueous ammonia. Oxygen saturation was maintained at 20% by the addition of air at a rate of 1 volume/volume of medium/minute and with stirring. The glucose was initially introduced at a concentration of 2g/l. Additional glucose was then introduced continuously using a stock solution of 700 g/l glucose and 19.6 g/l $MgSO_4.7H_2O$. The rate of addition was 2.2 g of glucose/h.l of medium. After fermenting for 24 hours, the cells were recovered by centrifugation. The paste, with a solids content of 26%, was used directly for the immobilization.

950 g of cell pellet containing 26.0% by weight of dry cells were diluted in 571.5 g of a 1 mol/liter phosphate buffer solution. The dilution was performed at ambient temperature in a reactor fitted with a three-paddle helical stirrer. After dilution, the pH was 8.0.

The 1 mol/liter phosphate buffer solution was obtained by dissolving 165.5 g of $K_2HPO_4$ and 6.8 g of $KH_2PO_4$ in one liter of deionized water. The initial pH of this solution was 9.0.

164.6 g of an aqueous glutaraldehyde solution at 6% by weight was added slowly to the cell suspension. The mixture obtained was left stirring for a minimum of 1 hour at ambient temperature, before the addition of 395.2 g of an aqueous polyazetidine (Kymene 617) solution at 12.5% by weight. A cell suspension was thus obtained, the composition of which is summarized in Table 2 below:

TABLE 2

| Component | Solids Content (%) | Amount (g) | Dry weight (g) | % of the total | g dry/l of water (%) |
|---|---|---|---|---|---|
| Cell pellet | 26.0 | 950.0 | 247.0 | 11.9 | 14.7 |
| Phosphate buffer solution | 15.23 | 571.5 | 87 | 4.2 | 5.9 |
| Glutaraldehyde solution | 6.0 | 164.6 | 9.9 | 0.5 | 0.6 |
| Polyazetidine solution | 12.5 | 395.2 | 49.4 | 2.4 | 2.9 |
| TOTAL | | 2081.3 | 404.6 | 19.4 | |

1800 g of this cell suspension was sprayed onto 350 g of alumina beads 2.0 mm in diameter, which were fluidized in a stream of hot air (inlet temperature of 53° C.). The spraying rate was adjusted so as to keep the temperature of the beads at 35° C. After spraying for 170 minutes, 841 g of biocatalyst was obtained, containing 25.5% by weight of dry cells and 16.6% of residual water. The thickness of the coating was 330 microns. The diameter of the coated granule was 2.6 mm. The ratio of the size of the granule to the thickness of the coating was 7.

1.2 Catalytic Conversion of HMTBN to HMTBS.

The activity of this catalyst, measured at 25° C. at pH 6.6 in the presence of 0.1 mol/l of HMTBN, was 0.56 kg of HMTBN converted to 2-hydroxy-3-methylthio butanoate of ammonium (HMTBS) per hour and per kg of catalyst.

A thermostat column with an internal diameter of 3 cm and 45 cm in length was filled with 100 g of catalyst. The column was fitted with a pump via a re-circulation loop. The total volume of the reactor was 430 ml. The loop was filled with a 25% solution of the ammonium salt HMTBN. The solution was feed into the column at the top and passed to the bottom at a rate of 20 liters per hour. Water was circulated in a double envelope around the column to maintain the temperature at 35° C. Mineral water was introduced in the loop at rate of 40 grams per hour. The volume of the reactor was maintained at a constant level by removing excess liquid from the base of the column. A continuous flow was obtained with a conversion of 95% nitrile. The concentration of HMTBS leaving the reactor was 25%. The half-life at 35° C. in the presence of 0.2 moles/l HMTBN was 30 hours.

EXAMPLE 2

2.1 Preparation of the Enzymatic Catalyst.

1100 g of a cell pellet containing 26% by weight. of dry cells and prepared as described in Example 1 were diluted in 13.2 kg of a water solution containing 9 g/l of sodium chloride. The suspension was stirred at room temperature for 30 minutes in a well stirred tank reactor. The cells were recovered by centrifugation.

950 g of the washed cell pellet containing 26% by weight of dry cells were treated as described in Example 1 above resulting in 1800 g of a treated suspension. After spraying for 170 minutes, 850 g of catalyst was obtained, containing 25.5% by weight of dry cells and 17% of residual water. The thickness of the coating was 190 microns. The diameter of the core was 2.2 mm. The ratio of the size of the core to the thickness of the coating was 11.6.

2.2 Catalytic Conversion of HMTBN to HMTBS.

The activity and the half life of the catalyst was measured as described in example 1 at 35° C. at pH 6.6 in the presence of 0.1 mol/l of HMTBN. The activity was 0.5 kg of HMTBN converted to 2-hydroxy-3methylthio butanoate of ammonium (HMTBS) per hour and per kg of catalyst. The half life was 70 hours.

EXAMPLE 3

3.1 Preparation of the Enzymatic Catalyst:

The procedure of Example 1 was repeated except that a polymer matrix composed of 23% of polyethyleneimine and 77% of polyazetidine was used. The final composition of the cell suspension is summarized in the table below.

| Component | Solids Content (%) | Amount (g) | Dry weight | % of the total | g dry/l of water (%) |
|---|---|---|---|---|---|
| Cell pellet | 26.0 | 400.0 | 104.0 | 7.5 | 8.5 |
| Phosphate buffer solution | 6.9 | 600.0 | 41.4 | 3.0 | 3.4 |
| Glutaraldehyde solution | 3.0 | 139.0 | 4.2 | 0.3 | 0.3 |
| Polyazetidine solution | 5.0 | 208.0 | 10.4 | 0.8 | 0.9 |
| Polyethyleneimine solution | 8.0 | 39.0 | 3.1 | 0.2 | 0.3 |
| TOTAL | | 1386.0 | 163.1 | 11.8 | |

1300 g of this cell suspension was sprayed onto 400 g of alumina beads under the same operating conditions as in Example 2. After spraying for 130 minutes, 553 g of catalyst was obtained containing 17.6% by weight of dry cells and 7.5% of residual water. The thickness of the coating was 210 microns. The diameter of the core was 2.2 mm. The ratio of the size of the core to the thickness of the coating was 10.

The resulting catalyst was used in the conversion of HMTBN to HMTBS and gave similar results to the other catalysts described above.

EXAMPLE 4

4.1 Preparation of the Enzymatic Catalyst with Polyamidase Activity:

134 g of cell paste of recombinant *Escherichia coli* containing polyamidease activity, prepared as detailed in French Patent Application No. 9508916, herein incorporated by reference, was diluted in 230 g of phosphate buffer (0.2 M, pH8.0). The procedure as detailed in Example 3 was repeated and 540 g of the cell suspension was sprayed onto 400 g of alumina beads under the same conditions as detailed in Example 1.

4.2 Catalytic Hydrolysis of NYLON 66

The enzyme activity was measured according to the procedure on FR 95098016. The catalyst activity measured at 30° C. and at pH7 in the presence of 5 g/l of NYLON 6,6 oligomers was 140 g of NYLON 6,6 oligomers converted to adipic acid per hour and per liter of catalyst. The half life exceeded 790 hours.

Comparative Example A

A.1 Preparation of the Enzymatic Catalyst:

100 g a cell suspension prepared as described in Example 1 was sprayed on to 350 g of alumina beads 2.0 mm in diameter, which were fluidized in a stream of hot air (inlet temperature of 53° C.). The spraying rate was adjusted so as to keep the temperature of the beads at 35° C. After spraying for 170 minutes, 385 g of catalyst was obtained containing 3% by weight of dry cells. The thickness of the coating was 20 microns. The diameter of the core was 2 mm. The ratio of the size of the core to the thickness of the coating was 100.

A.2 Catalytic Conversion of HMTBN to HMTBS.

The activity and the half life of this biocatalyst was measured as described in Example 1 at 25° C. at pH 6.6 in the presence of 0.1 mol/l of HMTBN. The activity was 0.06 kg of HMTBN converted to 2-hydroxy-4-methylthio butanoate of ammonium (HMTBS) per hour and per kg of catalyst. The half life was 11 hours.

The invention claimed is:

1. An enzymatic catalyst in granular form which is insoluble in water, said catalyst comprising an inner core and a coating which coating comprises an enzymatic material, a polymer, a cross-linking agent and 0 to 30% water, wherein the coating has a thickness of from 100 to 250 microns and the ratio of the size of the core to the thickness of the coating is from 3 to 15.

2. An enzymatic catalyst as claimed in claim 1 in which the core is mesoporous or microporous.

3. An enzymatic catalyst as claimed in claim 1 in which the core is selected from the group consisting of alumina, silica, a zeolite, a resin, a fatty substance, a glass bead and a plastic bead.

4. An enzymatic catalyst as claimed in claim 1 in which the enzymatic material is selected from the group consisting of glucose isomerases, penicillin aceylases, nitrile hydratases, nitrilases, amideases, lipases, proteases and esterases.

5. An enzymatic catalyst as claimed in claim 4 in which the enzyme is a nitrilase.

6. An enzymatic catalyst as claimed in claim 1 in which the polymer is selected from the group consisting of polyazetidine polymers, polyamine polymers, polyamide polymers and isocyanate polymers and the cross-linking agent is selected from the group consisting of amines, aldehydes, acids and isocyanates.

7. An enzymatic catalyst as claimed in claim 1 in which the coating comprises a nitrilase, a polyazetidine polymer and glutaraldehyde.

8. An enzymatic catalyst as claimed in claim 1 having a half life of at least 30 hours.

9. A process for the preparation of a granular enzymatic catalyst as claimed in claim 1 which comprises forming a suspension of an enzymatic material, a polymer and a cross-linking agent and spraying said suspension onto the core, thereby coating said core.

10. A process as claimed in claim 9 wherein the enzymatic material is an enzymatically active cell sludge which has been washed prior to formation of the suspension.

11. An enzymatic catalyst as claimed in claim 1, wherein the catalyst has a half-life of at least 70 hours.

12. A method for converting 2-hydroxy-4-methylthio butyronitrile into ammonium 2-hydroxy-4-methylthio butanoate comprising the step of contacting the enzymatic catalyst as claimed in claim 1 with 2-hydroxy-4-methylthio butyronitrile.

* * * * *